United States Patent [19]
Hobbs et al.

[11] Patent Number: 5,584,821
[45] Date of Patent: Dec. 17, 1996

[54] SOFT TIP CATHETER

[75] Inventors: Eamonn Hobbs, Queensbury; William M. Appling, Hartford, both of N.Y.

[73] Assignee: E-Z-EM, Inc., Westbury, N.Y.

[21] Appl. No.: 496,221

[22] Filed: Jun. 28, 1995

Related U.S. Application Data

[63] Continuation of Ser. No. 892,261, Jun. 2, 1992, abandoned.

[51] Int. Cl.$^6$ ...................................................... A61M 25/00
[52] U.S. Cl. ........................... 604/280; 604/264; 604/282; 138/140
[58] Field of Search ...................... 604/280–282, 604/264, 265; 128/656–658; 427/2.1, 2.24, 2.25, 2.28, 2.3; 138/125, 137, 140, 141, 145, 146, 153

[56] References Cited

U.S. PATENT DOCUMENTS

| | | | |
|---|---|---|---|
| 4,563,181 | 1/1986 | Wijayarathna et al. | 604/280 |
| 4,842,590 | 6/1989 | Tanabe et al. | 604/282 |
| 4,886,506 | 12/1989 | Lovgren et al. | 604/282 |
| 4,898,591 | 2/1990 | Jang et al. | 604/282 |
| 4,994,047 | 2/1991 | Walker et al. | 604/264 |
| 5,078,702 | 1/1992 | Pomeranz | 604/282 |
| 5,085,649 | 2/1992 | Flynn | 604/282 |
| 5,160,559 | 11/1992 | Scovil et al. | 604/280 |
| 5,221,270 | 6/1993 | Parker | 604/280 |
| 5,234,416 | 8/1993 | Macaulay et al. | 604/282 |
| 5,300,032 | 4/1994 | Hibbs et al. | 604/264 |
| 5,322,659 | 6/1994 | Walder et al. | 604/265 |

*Primary Examiner*—Corrine M. McDermott
*Assistant Examiner*—Ronald K. Stright, Jr.
*Attorney, Agent, or Firm*—McAulay Fisher Nissen Goldberg & Kiel, LLP

[57] ABSTRACT

An angiographic catheter has a relatively stiff though flexible shaft and a soft tip. The soft tip consists primarily of a tungsten loaded polyether block amide (PEBA) copolymer surrounded by two thin PEBA layers. This three ply radiopaque tip is bonded to a PEBA shaft. The shaft is reinforced either by a inner nylon ply or by metal braiding.

19 Claims, 2 Drawing Sheets

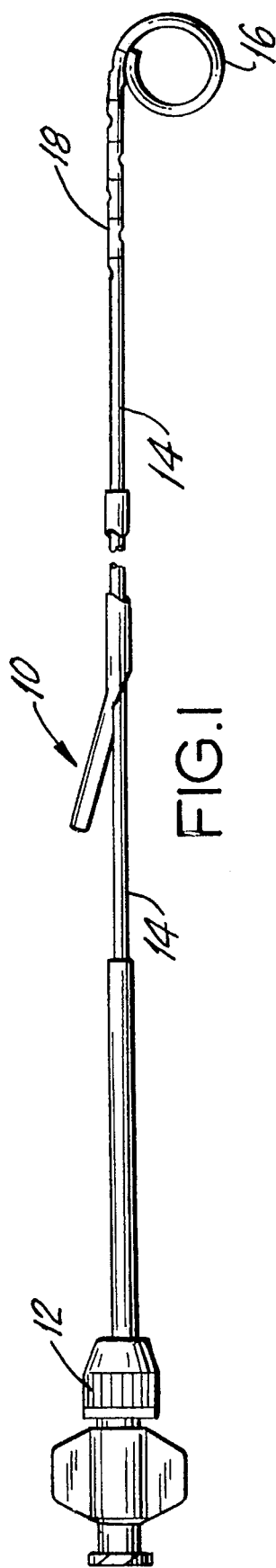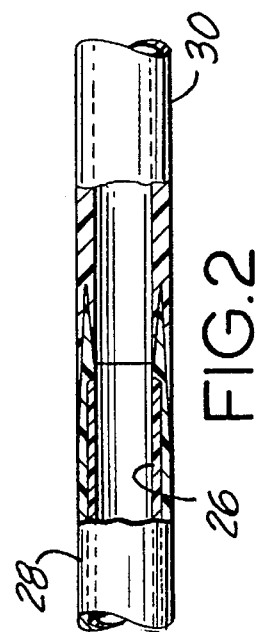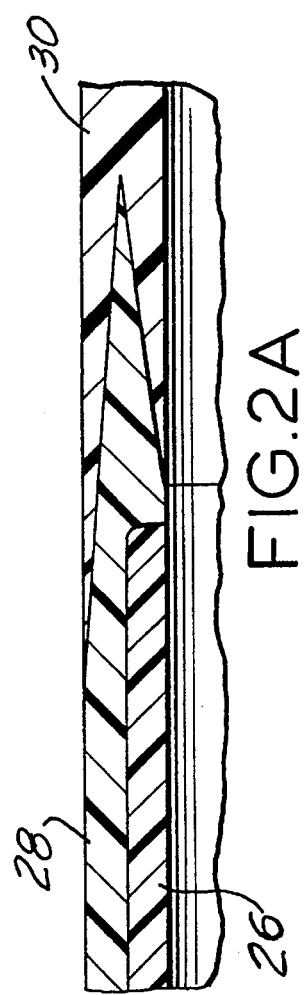

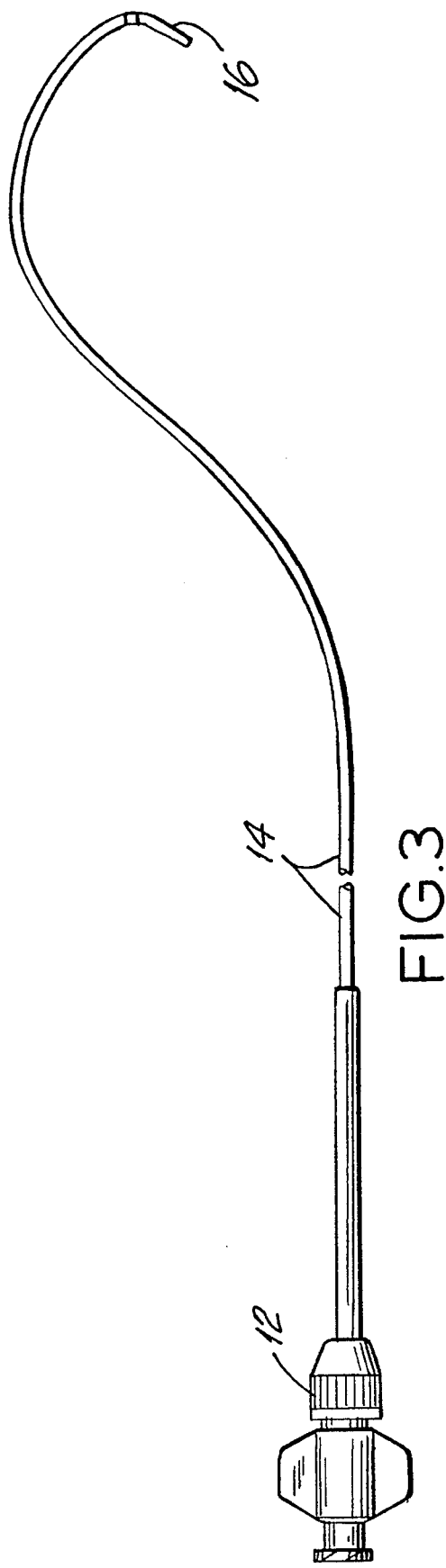
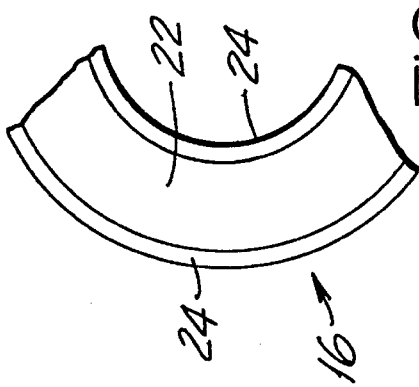
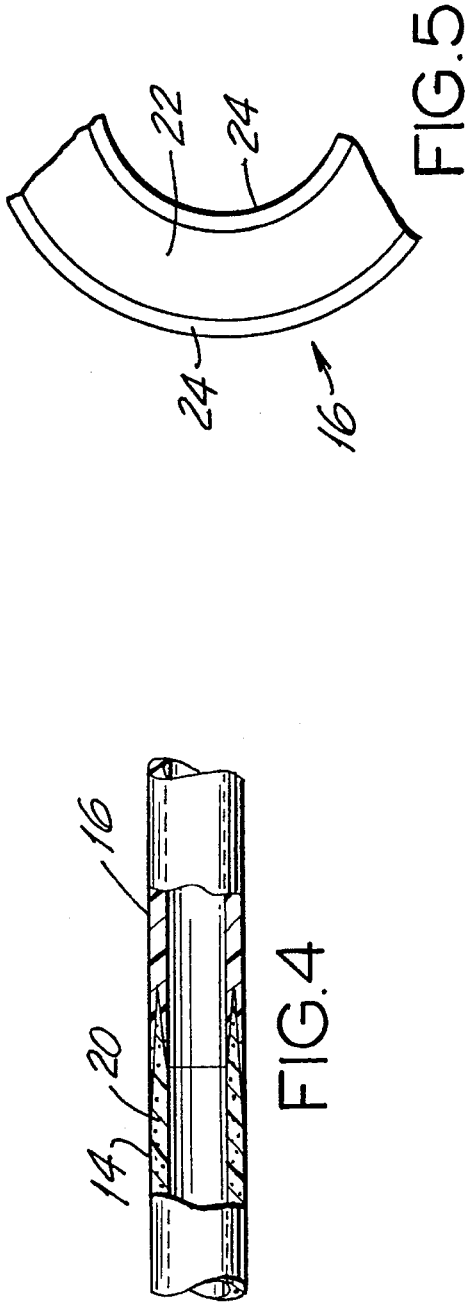

5,584,821

SOFT TIP CATHETER

This is a continuation of application Ser. No. 07/892,261 filed Jun. 2, 1992 now abandoned.

BACKGROUND OF THE INVENTION

This invention relates in general to intravascular catheters and more particularly to a catheter that is inserted into and through blood vessels for the purpose of injecting radiopaque substances to aid in the imaging of blood vessels and organs. Such catheters are called angiographic catheters.

It is known to incorporate a soft tip in the leading or distal end of these catheters to avoid injury to the walls of the blood vessels. The body of the catheter, however, has to be relatively stiff to withstand the pressure of the radiopaque material being delivered through the catheter and to provide enough torqueability so that the tip, usually curved, can be directed through the blood vessel.

A known type of soft tip catheter is disclosed in U.S. Pat. No. 4,563,181 issued on Jan. 7, 1989 to Wijayarathna and Hopkins. The patent provides a useful description of the prior art and of the need for the combination of a soft tip portion and a stiff body portion. To properly locate the catheter in the patient, it is important that the distal end of the catheter be sufficiently radiopaque so as to make it readily visible on the fluoroscopy screen.

Polymer materials and in particular nylons of great structural strength have become available which make it possible to design very thin wall catheters to withstand high pressure without bursting. Pressures of up to 1,200 psi have to be withstood by the catheters in use. Because of these very thin wall sections, it is now possible, to produce a 5 French catheter with inside diameters that exceed the inside diameters of old style 6 French catheters. However, these extremely thin wall catheters, which can be in the range of 8 to 11 mils (0.008 to 0.010 inches) in wall thickness, provide such small sidewall thickness that it is difficult to view and guide the catheter under fluoroscopy.

Accordingly, a purpose of this invention is to provide a soft tip and relatively stiffer body angiographic catheter with enhanced visibility under fluoroscopy.

Because of the thin sidewall and the high pressures, it is important that the soft material of the tip bond with sufficient strength to the flexible, though relatively stiff material of the body to avoid detaching the tip under internal catheter pressure.

Accordingly, it is another purpose of this invention to provide a highly radiopaque tip which has a high bonding strength to the catheter body.

From the point of view of tissue trauma and damage, it is useful to have as small an outside diameter (O. D.) catheter as possible. Since the inside diameter is essentially dictated by the amount and rate of liquid that has to be injected, the thinner the wall, the smaller the O. D.

Accordingly, there is a trade-off between small wall thickness, high burst strength and visibility under fluoroscopy. It is a significant object of this invention to provide a soft tip angiographic catheter design which provides an enhanced trade-off of these parameters.

BRIEF DESCRIPTION

In brief, the angiographic catheters disclosed have a relatively stiff though flexible shaft together with a soft tip segment. The soft tip is composed of a sandwich consisting of an inner and outer coat of polymer material surrounding a core layer consisting of a polymer material which is highly loaded with a radiopaque material.

The shaft can be either a metal braided reinforced polyether block amide (PEBA) copolymer or a co-extruded two ply wall consisting of nylon and PEBA copolymer. In the latter case, the nylon provides the stiffness and burst resistance. In the former case, the metal braiding provides the desired stiffness and burst strength.

The inner and outer plies or coating of the tip is a PEBA copolymer material while the radiopaque core is a PEBA copolymer which is loaded with, in one example, 67.5 percent by weight of tungsten powder.

The PEBA copolymer of the tip bonds well to the PEBA copolymer of the shaft to provide the desired resistance to rupture at the juncture between shaft and tip.

BRIEF DESCRIPTION OF THE DRAWINGS

FIG. 1 is a longitudinal view of a first embodiment of a catheter of this invention showing a typical curled soft tip and a shaft with openings adjacent to the tip.

FIG. 2 is a longitudinal cross-section of a segment of the FIG. 1 catheter in a somewhat stylized form, illustrating the zone where the tip and sidewall are bonded together. The FIG. 2 catheter is one where the shaft sidewall is a co-extruded two ply material, the inner ply being nylon and the outer ply being PEBA copolymer.

FIG. 2A is a larger scale view of a section through the catheter wall showing the bonding zone between shaft PEBA 28 and tip PEBA 30.

FIG. 3 is a longitudinal view of a second embodiment showing a typical curved tip.

FIG. 4., like FIG. 2, is a stylized longitudinal cross-section of the zone of the catheter where the tip bonds to the shaft. FIG. 4, however, illustrates the embodiment where the shaft sidewall consists of a metal braid embedded in a PEBA copolymer wall.

FIG. 5 is a larger scale cross-sectional view through a portion of the tip sidewall showing the radiopaque center ply 22 surrounded by the inner and outer pure PEBA plies 24.

It should be noted that in FIGS. 2 and 4, the longitudinal cross-section through the soft tip does not distinguish between the inner and outer plies and the central ply because the inner and outer plies are such thin coats on the central radiopaque ply that showing them even schematically would excessively distort the dimensional relationships and thicknesses that are illustrated in these figures.

DESCRIPTION OF THE PREFERRED EMBODIMENTS

As shown in the FIGS., a catheter 10 with a standard proximal luer 12 has a shaft 14 which terminates at a soft tip 16.

In the FIG. 1 embodiment, at the portion of the shaft 14 adjacent to the soft tip 16 there are a series of openings 18 which are used to deliver radiopaque dye to the organ or tissue of the patient into which the catheter 10 is threaded.

In the FIG. 3 embodiment, the sidewall 14 contains a known type of metal braiding 20 which serves to stiffen the sidewall. This reinforcing braid is a known technique and is disclosed, for example, in U.S. Pat. No. 4,898,591 as the braid 34 shown in FIG. 2 thereof and discussed at column 5, lines 15 through 22 therein. In the FIG. 3 embodiment, the material in which the braid 20 is encased is a known type of polyether block amide (PEBA) copolymer.

In both embodiments, the soft tip 16 is a highly radiopaque element composed of fine tungsten powder embedded in a PEBA copolymer. A tungsten/PEBA core ply 22 is contained between two thin unfilled plies 24 of PEBA of the same type as employed in the core ply. The tip 16 is made as a triple layer extrusion. The unfilled PEBA surface plies 24 provide a smooth inner and outer surface. Yet the tip 16 itself has relatively high visibility under fluoroscopy.

In one embodiment, the tungsten powder has a mean average diameter of between one and two microns and the core ply 22 is 80 percent of the tip sidewall thickness while each surface ply 24 is ten percent of tip wall thickness. The tungsten constitutes between 65 and 70 percent by weight of the core ply. Yet the PEBA copolymer is about 90 percent by volume of the core ply 22. Thus a substantial amount of tip PEBA is available for bonding to the shaft PEBA.

As is known in the art, the braid reinforcement embodiment of FIG. 4 is used to provide a greater torque and is used in what are called selective catheters which have no or few side holes. The selective catheters are designed to access a specific artery and require considerable control by the physician and are intended to deliver relatively small amounts of contrast media. By contrast, the FIG. 2 co-extruded sidewall catheter design with a nylon ply reinforcement tends to be used as a flush catheter to deliver a higher bolus of contrast media at a high pressure. The flush catheter employs a larger number of exit openings 18 for the contrast media.

A No. 4 french (4F) embodiment will have an outside diameter of 54 mils and an inside diameter of 38 mils thereby having a sidewall thickness of 8 mils. A 5F embodiment will have an O.D. of 67 mils and an I.D. of 48 mils thereby having a sidewall thickness of 9.5 mils. A 6F embodiment will have an O.D. of 79 mils and an I.D. of 57 mils thereby having a sidewall thickness of 11 mils. In the FIG. 2 embodiment, the sidewall is composed of two plies approximately equal in thickness. In the 4F embodiment, the nylon ply is 4 mils and the PEBA ply 4 mils, in the 5F embodiment, the nylon ply is 5 mils and the PEBA ply is 4.5 mils. In the 6F embodiment, the nylon ply is 6 mils and the PEBA ply is 5 mils.

The proximal end of the tip 16 has the same diameters and wall thickness as does the shaft. However, the tip typically necks down toward its distal end.

As shown in the schematic FIG. 2A, the bonding of tip 16 to shaft 14 is essentially between the PEBA copolymers of the tip and the shaft. These PEBA copolymers being of a similar chemical composition and similar melting points create an effective bond which is not available between nylon and PEBA. In this fashion, the nylon ply 26 provides the required shaft stiffness and torqueability. The PEBA ply 28 provides the basis for effective bonding between shaft and tip.

Accordingly, by a combination of (a) PEBA shaft material, (b) PEBA tip material, (c) highly radiopaque particles embedded in the PEBA tip with (d) a smooth unfilled PEBA coating on the inside of the tip and (e) appropriate reinforcement of the PEBA shaft, applicant has put together structural features which provide an optimum trade-off of functional results; namely, a thin shaft wall with good bonding between tip and shaft and visibility of tip under fluoroscopy.

The Bonding Process

The process that joins the shaft 14 and tip 16 produces a finger joint style weld. This finger joint weld is illustrated in FIGS. 2 and 4 and is best seen in FIG. 2A. The relatively large area of bonding between shaft PEBA and tip PEBA provides a strong bond. The technique for producing this result involves placing a slip fit teflon coated metal mandrel into the distal end of the shaft and stretching the proximal end of the tip over the distal end of the shaft over a length of approximately 1.5 to 2.0 millimeters (mm). Then a teflon sleeve is placed around the area to be bonded to create pressure between sleeve and mandrel. A radiant heat coil around the zone to be bonded provides radiant heat which causes the PEBA to melt under pressure and to flow into the configuration shown in FIGS. 2 and 4 in which the tip PEBA flows around the shaft PEBA and shaft PEBA is squeezed into the tip PEBA to form the finger type of joint shown.

It is believed that this large area finger joint bonding where tip PEBA flows around both sides of shaft PEBA is achieved in an effective manner because of a combination of three factors; namely (a) the chemical similarity of the PEBA copolymers in the shaft and tip, (b) the heat conductivity of the tungsten in the tip, and (c) a slightly lower tip PEBA melting point.

The melting point of the somewhat softer tip PEBA is lower by perhaps twenty degrees Fahrenheit than the somewhat harder PEBA used in the shaft. The PEBA in the tip will flow around the PEBA in the shaft and, because of the pressure, the PEBA in the shaft will flow into the center of the PEBA in the tip. The result, therefore, is that the tip PEBA extends along the outside surface of the shaft by approximately 1.5 mm and the shaft PEBA extends into the tip PEBA by a small distance so that some tip PEBA extends along the inner surface of the shaft PEBA.

In the FIG. 2 arrangement, the PEBA tip is fused to a shaft that has an inner ply of nylon and an outer ply of PEBA copolymer. The fusing under heat and pressure does not cause the nylon ply 26 to melt or change its dimensional characteristic. However, the shaft PEBA ply 28 and the tip PEBA material both melt sufficiently to form the finger joint. Because the nylon ply 26 does not melt, tip PEBA 30 does not flow along the inside of the shaft but only along a portion of the outside of the shaft.

Nonetheless in the FIG. 2 embodiment, like the FIG. 4 embodiment, there is a substantial surface fusion contact between the tip and shaft PEBA copolymers thereby providing an effective bond that resists failure under internal catheter pressure and resists being separated when the catheters are subject to tension.

Although two embodiments of this invention have been disclosed in detail, there are variations which can be made and still be within the scope of this invention as taught in the specification as set forth in the claims. For example, other highly radiopaque fillers could be used for the tip such as depleted uranium.

What is claimed is:

1. In an intravascular flexible catheter having a tubular shaft containing a reinforced polyether block amide (PEBA) copolymer ply, the improvement consisting essentially of:

a soft flexible radiopaque tubular tip distal of and bonded to said shaft, said tip having a sidewall with inner, outer and intermediate plies, said intermediate tip ply formed from a PEBA material embedded with radiopaque particles, said inner and outer plies being formed from an unfilled PEBA copolymer, said inner and outer plies providing a smooth inner and outer surface for said tip, said inner and outer plies constituting a coating on said intermediate ply and being a small fraction of the overall thickness of said intermediate ply.

2. The catheter of claim 1 wherein:

said radiopaque particles are tungsten.

3. The catheter of claim 2 wherein:

said intermediate tip ply has a thickness that is approximately eighty percent of the thickness of said sidewall of said tip.

4. The catheter of claim 3 wherein:

said tungsten constitutes approximately sixty-five to seventy percent by weight of said intermediate tip ply.

5. The catheter of claim 4 wherein:

said PEBA of said intermediate tip ply constitutes approximately ninety percent by volume of said intermediate tip ply.

6. An intravascular flexible catheter consisting essentially of:

a tubular shaft containing a reinforced polyether block amide (PEBA) copolymer ply, a soft flexible radiopaque tubular tip distal of and bonded to said shaft, said tip having a sidewall with inner, outer and intermediate plies, said intermediate tip ply formed from a PEBA material embedded with radiopaque particles, said inner and outer plies being formed from an unfilled PEBA copolymer, said inner and outer plies providing a smooth inner and outer surface for said tip, said inner and outer plies constituting a coating on said intermediate ply and being a small fraction of the overall thickness of said intermediate ply.

7. The catheter of claim 6 wherein:

said radiopaque particles are tungsten.

8. The catheter of claim 7 wherein:

said intermediate tip ply has a thickness that is approximately eighty percent of the thickness of said sidewall of said tip.

9. The catheter of claim 8 wherein:

said tungsten constitutes approximately sixty-five to seventy percent by weight of said intermediate tip ply.

10. The catheter of claim 9 wherein:

said PEBA of said intermediate tip ply constitutes approximately ninety percent by volume of said intermediate tip ply.

11. the catheter of claim 9 wherein:

said tubular shaft is reinforced by a nylon ply.

12. The catheter of claim 9 wherein:

said PEBA copolymer of said shaft has a hardness and a melting point greater than the respective hardness and melting point of said PEBA copolymer of said tip.

13. An intravascular catheter comprising:

a flexible tubular shaft having a sidewall, a soft flexible radiopaque tubular tip distal of and bonded to said tubular shaft, said tubular shaft having a reinforced polyether block amide (PEBA) copolymer ply, said tip having a sidewall with inner, outer and intermediate plies, said intermediate tip ply formed from a PEBA material embedded with radiopaque particles, said outer and inner tip plies being formed from an unfilled PEBA copolymer, said outer and inner plies providing a smooth inner and outer surface for said tubular tip, said outer and inner plies constituting a coating on said intermediate ply and being a small fraction of the thickness of said intermediate ply, said outer, intermediate and inner plies being the sole plies of said tip.

14. The catheter of claim 13 wherein:

said radiopaque particles are tungsten.

15. The catheter of claim 14 wherein:

said intermediate tip ply has a thickness that is approximately eighty percent of the thickness of said sidewall of said tip.

16. The catheter of claim 15 wherein:

said tungsten constitutes approximately sixty-five to seventy percent by weight of said intermediate tip ply.

17. The catheter of claim 16 wherein:

said PEBA of said intermediate tip ply constitutes approximately ninety percent by volume of said intermediate tip ply.

18. The catheter of claim 13 wherein:

said tubular shaft is reinforced by a nylon ply.

19. The catheter of claim 13 wherein:

said PEBA copolymer of said shaft has a hardness and a melting point greater than the respective hardness and melting point of said PEBA copolymer of said tip.

* * * * *